(12) United States Patent
Muller

(10) Patent No.: US 6,612,767 B2
(45) Date of Patent: Sep. 2, 2003

(54) SUBSTANCE APPLYING APPARATUS

(75) Inventor: Frank Muller, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 10/114,203

(22) Filed: Apr. 2, 2002

(65) Prior Publication Data

US 2002/0154936 A1 Oct. 24, 2002

Related U.S. Application Data

(60) Provisional application No. 60/315,564, filed on Aug. 29, 2001.

(30) Foreign Application Priority Data

Apr. 20, 2001 (DE) .......................................... 101 19 480

(51) Int. Cl.$^7$ ................................................ A45D 33/00

(52) U.S. Cl. ...................... 401/130; 401/123; 401/119; 401/132; 604/1; 604/3

(58) Field of Search ............................ 401/130, 40, 41, 401/42, 43, 132, 133, 139, 135, 123, 124, 126, 129; 604/1, 3

(56) References Cited

U.S. PATENT DOCUMENTS 6,450,717 B1 * 9/2002 Salz et al. .................. 401/125
RE37,931 E * 12/2002 Gueret ....................... 401/126
6,503,013 B2 * 1/2003 Strauss ....................... 401/123

FOREIGN PATENT DOCUMENTS

| DE | 20 24 402 | 12/1971 |
| DE | 44 15 854 A1 | 4/1995 |
| DE | 92 18 949 U1 | 7/1996 |
| DE | 199 56 705 A1 | 6/2001 |

* cited by examiner

Primary Examiner—David J. Walczak
(74) Attorney, Agent, or Firm—John C. Thompson; Alan S. Korman

(57) ABSTRACT

A substance applying apparatus for applying a substance to an application location. An application element having a wetting body is partially received in an inner tube and the inner tube is received in an outer tube. A fluid connection between the inner space of the inner tube and the inner space of the outer tube is produced by the application of pressure on the substance applying apparatus. The inner tube is comprised of a softer material than the outer tube and at least the bottom of the inner tube is deformable upon the application of pressure on the substance applying apparatus.

9 Claims, 3 Drawing Sheets

SUBSTANCE APPLYING APPARATUS

CROSS-REFERENCE TO RELATED APPLICATIONS

This application claims foreign priority benefits under 35 U.S.C. §119(a)–(d) from German patent application ser. no. 101 19 480.3-24 filed Apr. 20, 2001. In addition, this application claims the benefit under 35 U.S.C. §119(e) of U.S. provisional patent application ser. No. 60/315,564 filed Aug. 29, 2001.

BACKGROUND OF THE INVENTION

The present invention relates to a substance applying apparatus. It has long been known, with respect to the application of substances, to hold in readiness a first component of the substance in a first chamber and an additional component of the substance in a second chamber and to effect mixing of the two components in the two chambers by applying a pressure such that a structure adapted to maintain the two components separate from one another is broken through to thereby permit mixing of the two components within the two chambers. An example of such an arrangement is disclosed in DE-AS 2 024 402.

Substance applying apparatus having application elements have, in any event, long been known, whereby, for example, such a device is disclosed in DE-GM 92 189 49. Via side holes in an inner tube, a fluid connection between the inner space of the inner tube and the inner space of the outer tube is produced. This arrangement is suitable for cosmetic products. If the application scenario requires storage of the substance component in the inner space of the inner tube separate from the substance component in the inner space of the outer tube, however, this solution is less suitable.

It is further known in DE-OS 44 158 54 to provide a mixing and application capsule for dental purposes. With this arrangement, the substance components are united with one another by the puncture, with a sharp element, of a film between the substance components.

Numerous other substance applying apparatus are known. Thus, for example, it has been proposed to maintain an application element in a submerged condition in a fluid, whereupon, upon application of a downward pressure on the fluid retaining container, an additional fluid is permitted to flow thereinto in the manner of an overspill action, in order to thereby place in readiness the substance which is to be applied. This arrangement requires, in any event, two separate sealing off systems so that a not inconsiderable effort is required to configure the arrangement. A plurality of sealing locations brings with it, in any event, a correspondingly large susceptibility to damage and storage instability.

It has further been proposed, in German Patent Application 199 56 705.0, to dispose an application element with a wetting body partially in an inner tube and to dispose the inner tube in an outer tube. By means of an application of pressure on the application element, a fluid connection between the inner space of the inner tube and the inner space of the outer tube is produced. The arrangement basically offers a good and simple sealing off of the two substance components to be held in readiness for eventual combination together to form the substance to be applied. To be sure, the outer tube must be produced with a somewhat elastic material in preparation for the deployment of a sealing lip, in order to ensure a fluid tight disposition of the sealing lip between the inner tube and the outer tube. On the other hand, it is important that the substance to be received in the inner space of the outer tube can also be stored therein in a secure manner for a long time. In order to achieve this goal, a substantially large wall thickness must be provided.

In certain applications, additionally, solvents such as acetone, ethyl alcohol and so forth are deployed as the substance components. Such solvents exhibit an exceptionally high vapor pressure and diffuse through the outer tube, even if the walls thereof have a substantially large wall thickness.

To be sure, it has become conventionally known to limit a high vapor pressure by the addition of additional coatings such as, for example, a metallic coating. The problem with this arrangement is that double-coated materials are problematic due to the processing and disposal issues involved therewith and, moreover, a complete blocking off of the vapor pressure is not possible. To be sure, the metallic coating can also be applied on an interior surface. In that event, however, the metallic coating extends over the sealing lips disposed therein so that the sealing effect is thereby reduced. At the same time, the application of a metallic coating adds to the production expense of the substance applying apparatus, whereby the production costs of such devices in connection with the realization of a single dose unit is of particular importance.

SUMMARY OF THE INVENTION

The present invention offers a solution to the challenge of providing a substance applying apparatus which is cost favorable in its production and which is operable to apply a substance, with the substance applying apparatus being suitable as well for storing the to be applied substance components therein for more than one year and for applying substances having a high vapor pressure.

In accordance with the present invention, it is especially advantageous that the formation of the inner tube of a soft material permits the sealing off function to be ensured solely by the inner tube itself and permits the formation of the outer tube from a non-yielding and highly non-porous material. This arrangement is cost favorable for the reason that the wall thickness of the outer tube can be reduced while, however, storage stability is available due to the improved vapor pressure sealing off ability.

The desired softness and deformability of the inner tube, in accordance with the present invention, permits flexibility in the material choices as well as the configuration choices of the inner tube. If a deformation element exerts a one-sided radial force on the bottom of the inner tube or on a region adjacent to the bottom of the inner tube, the inner tube collapses thereat, at least partially, so that the sealing off between the inner tube and the outer tube is lost in the desired manner.

In accordance with the present invention, it is preferable if the sealing lip is formed in an annular shape in the region adjacent the bottom of the inner tube and extends outwardly. The wall of the outer tube can thereby be formed, in the interior of the outer tube, with a completely smooth surface up to the location of the deformation element.

In accordance with the present invention, it is particularly advantageous if the bottom of the inner tube is configured to be significantly thin. Due to a one-sided and massive wedge, which forms the deformation element, a correspondingly thin bottom of the inner tube can be deformed in the application operation, even if the material properties of the substance components in the inner tube and the outer tube differ only slightly from one another. To this extent, the formulation of a tube to be "softer" is also to be understood to include the concept of being "more yielding" and, as required, the inner tube can alternatively be comprised of a substantially hard material, it being understood that the prerequisite therefor is that the desired sealing off function must still be ensured.

In accordance with a particularly favorable embodiment of the substance applying apparatus of the present invention, the deformation element or the deformation body is disposed on the side of the inner wall of the outer tube and extends in a progressively sharper manner in the direction toward the bottom of the inner tube. The radial depth of the deformation element increases continuously in a direction toward the bottom of the outer tube and, in the region of the inner tube, approaches substantially zero radial depth. In this manner, the resistance of the inner tube to insertion along the deformation element is substantially small and the deformation of the inner tube occurs in a gradual manner as the inner tube is inserted downwardly.

The deformation element, on its outer side can either be ball shaped or have a cutting portion. In the configuration of the deformation element with a cutting portion, it is also possible to exploit the hard material properties of the outer tube such that the bottom of the inner tube, or especially, one or more sealing rings, are normally cut. In this arrangement, the openings in the inner tube can be dispensed with, whereby it is to be understood that suitable desired deformation elements can be deployed in order to produce a fluid connection between the inner space of the inner tube and the inner space of the outer tube.

It is also possible to configure the sealing ring as an O-ring which is disposed in a groove on the inner tube. In this arrangement, the cutting portion can cut the O-ring. The O-ring retracts along its longitudinal extent and thereby makes available for fluid passage therethrough a region in which the fluid can flow through the openings into the inner space of the inner tube.

It is to be understood that the groove should be so configured that the cutting operation of the cutting portion is not hindered but, instead, is facilitated.

Even in the event that an asymmetric deformation element is preferred, it is possible without additional structure to provide two deformation bodies disposed in opposed arrangement to one another and cooperating together to pinch the inner tube and thereby produce a space or gap in the form of an overflow channel between the inner space of the inner tube and the inner space of the outer tube. It is additionally further possible, without additional structure, to configure the deformation body in a suitable desired configuration, whereby it is preferred that an inner corner extends immediately adjacent the deformation body which permits an overflow to flow therealong toward the bottom of the inner tube.

The application element comprises a wetting body which, as required, is either already provided with a reaction substance, or is provided with a reaction substance before the application operation. The wetting body can be configured in a suitably desired manner as, for example, a brush or a foam body which is connected or coupled to a stock of the application element.

It is also possible that the application element is itself separately deployed and thus a different combination of substance components can be placed in readiness for subsequent mixing together to form the substance to be applied, whereby advantage can be taken of the fact that the substance applying apparatus can also be sealed off without an application element therein.

Further advantages, details and features are described in the hereinafter-following description of an embodiment of the substance applying apparatus of the present invention taken in connection with the figures of the drawings.

BRIEF DESCRIPTION OF THE DRAWINGS

The object and advantages of the present invention will appear more clearly from the following specification in conjunction with the accompanying schematic drawings, in which.

DETAILED DESCRIPTION OF THE PREFERRED EMBODIMENTS

Figure 1:
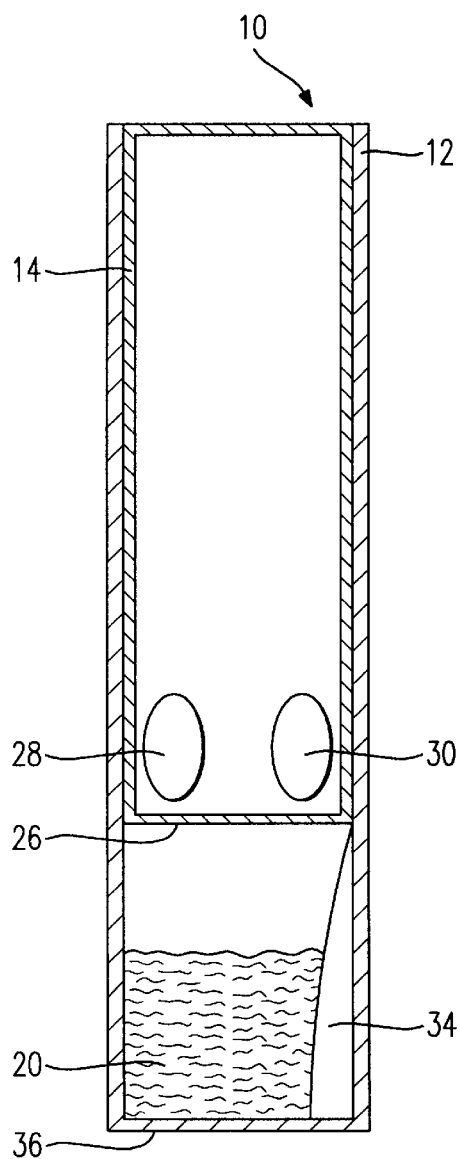
FIG. 1 is a generally schematic view of one embodiment of the substance applying apparatus of the present invention whereby the application element has been omitted and whereby the inner tube is disposed in an outward condition relative to the outer tube.

As seen in FIG. 1, one embodiment of the substance applying apparatus of the present invention, hereinafter, the substance applying apparatus 10, comprises an outer tube 12 which forms a housing. An inner tube 14 is guided within the substantially flask or bucket-shaped outer tube and is configured in a special manner in accordance with the present invention. The inner tube 14 is particularly configured to receive therein an application element 16, which can be seen in FIG. 2, and which is provided with a wetting body 18.

The outer tube 12 is longer than the inner tube 14 and is provided, in its bottom region, with a fluid 20 which is available for the preparation of the substance to be applied.

The inner tube 14 seals off an area or region of the outer tube 12—namely, the inner space of the outer tube. The inner tube 14 comprises in this connection a sealing lip 24 (see FIG. 6) which extends in an annular manner and is disposed adjacent the bottom 26 of the inner tube 14. The inner tube 14 is, in the illustrated embodiment, comprised of plastic and the outer tube 12 is comprised of glass. The sealing lip 24 can seal off the smooth inner wall of the outer tube 12 in a good seal-tight manner.

The inner tube 14 comprises two relatively large openings 28 and 30 which extend in a side-wise manner along the wall of the inner tube to a location adjacent the bottom 26 of the inner tube. These openings permit the easy and rapid through flow of the fluid 20 upon the insertion of the inner tube 14 into the outer tube 12.

Figure 5:
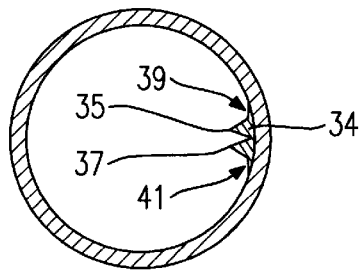
FIG. 5 is a top plan sectional view of a deformation element in the arrangement of the outer tube.

A deformation element 34 is provided to effect a fluid connection between the inner space of the inner tube 14 and the inner space of the outer tube 12. The deformation element 34 is, in the illustrated embodiment, configured as wedges and has the configuration as shown in FIG. 5. The wedges extends from the bottom 26 of the inner tube 14, in the condition thereof shown in FIG. 1, to the bottom 36 of the outer tube 12.

Figure 2:
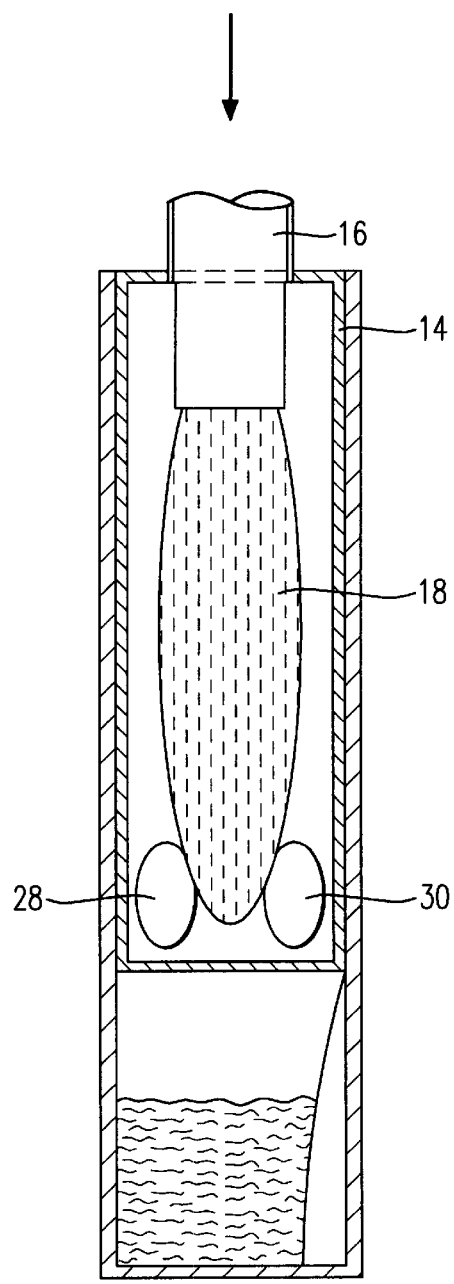
FIG. 2 is a sectional view of the one embodiment of the substance applying apparatus shown in FIG. 1, whereby the application element has been inserted into the tube.
Figure 3:
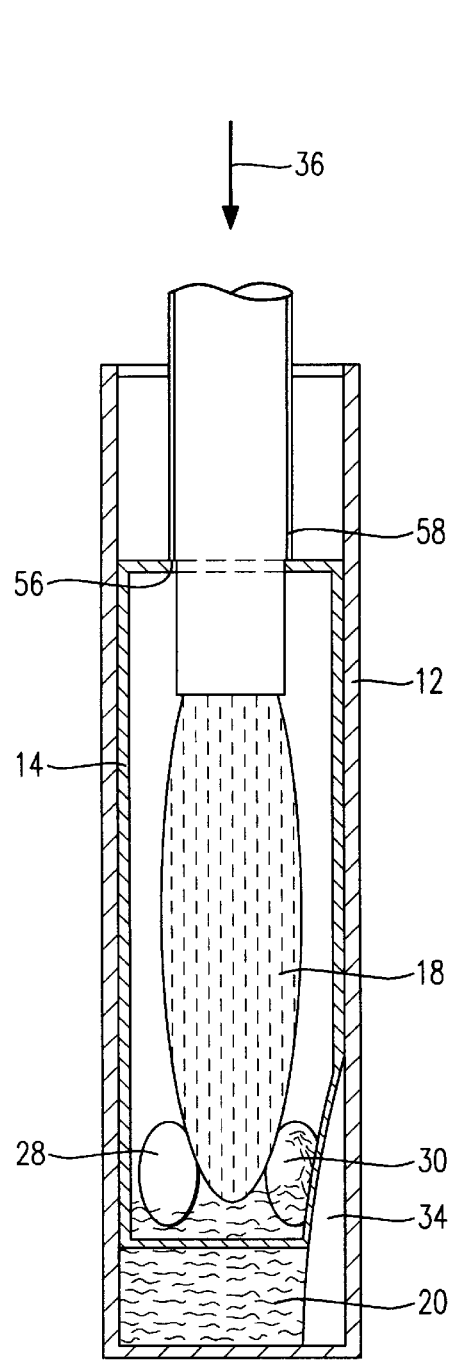
FIG. 3 is a sectional view of the one embodiment of the substance applying apparatus shown in FIGS. 1 and 2, whereby a pressure has already been exerted on the application element and the inner tube has been inserted into the outer tube, the inner tube being asymmetrically deformed at least to the openings.

While FIG. 2 shows the manner in which the application element 16 with the wetting body 18 is inserted into the inner tube, FIG. 3 shows the overflow of the fluid 20 into the inner tube 14. The inner tube 14 is moved at the same time into the outer tube 12 due to the application of pressure on the application element 16 in the direction of the wedge 36 as shown in FIG. 3. In this connection, the inner tube comprises an engagement shoulder 56, which has a diameter which is somewhat less than the diameter of a sealing periphery 58 of the application element 16. It is thus possible to exert pressure in this manner on the inner tube 14 without the necessity for a pointed element 54 to contact the bottom 26 of the inner tube.

Figure 4:
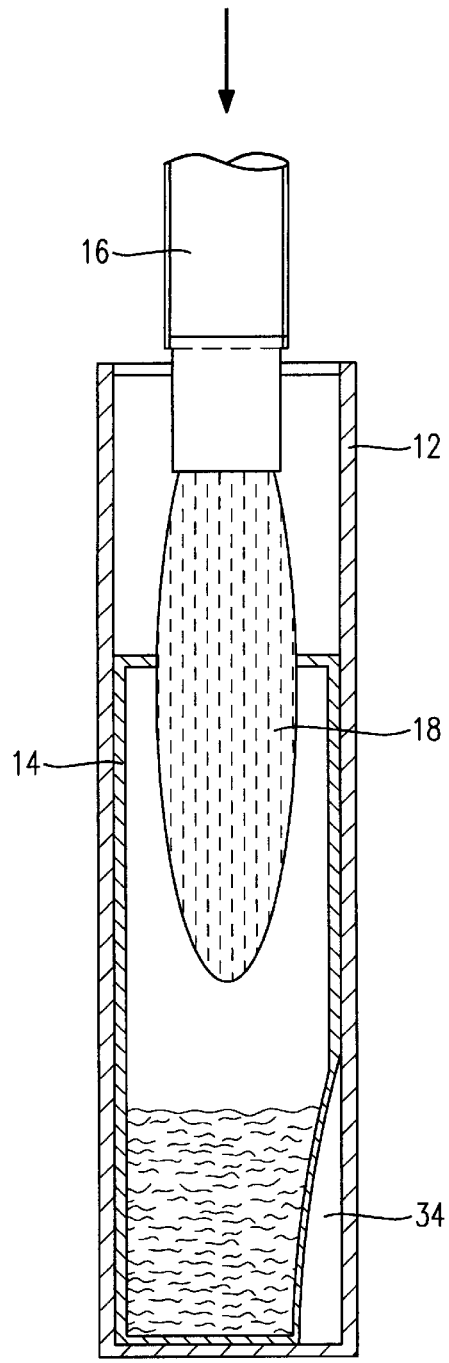
FIG. 4 is a sectional view of the one embodiment of the substance applying apparatus shown in FIGS. 1–3, whereby the inner tube has been completely inserted into the outer tube and the wetting body of the application element has been wetted with the substance.

As can be seen in FIG. 4, the wetting body 18 is intensively wetted with the substance 20 and the substance 20 is applied via the application element 16. In this operational condition, the substance applying apparatus 10 forms a bucket configuration for the application of the substance, whereby multiple immersions of the wetting body 18 are possible without further structure.

FIG. 5 shows the particular manner in which the deformation element can be configured. In the illustrated embodiment, the deformation element 34 has two substantially wedge-shaped portions with two points or apexes 35 and 37, which makes possible a reduced sliding resistance upon the sliding thereover of the bottom 26 of the inner tube 14 along the deformation element 34. It can be seen that the deformation element is provided along its sides with inner corners 39 and 41, which make possible an easy flow through of a substance through the gap between the outer wall of the inner tube and the inner wall of the outer tube, and then into the inner space of inner tube 14.

Figure 6:
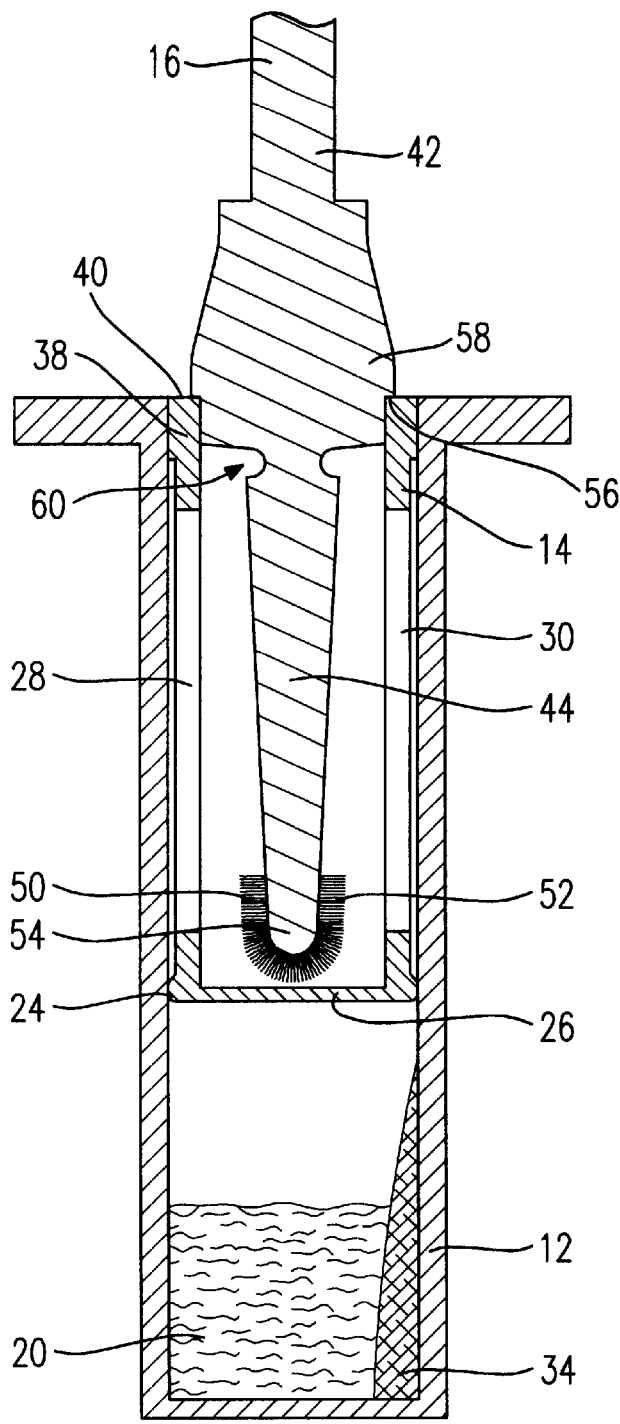
FIG. 6 is a schematic view of another embodiment of the substance applying apparatus of the present invention.

In FIG. 6, another embodiment of the substance applying apparatus of the present invention is illustrated. In this embodiment, the inner tube 14 comprises a sealing off ring 38, from which a projection 40 extends outwardly. A sealing lip is formed thereat such that a sealing off is ensured upon the disposition of the application element 16 therein.

The application element 16 includes a grip 42. The grip 42 extends into a thickened portion 58, which is connected with a shaft 44. In this embodiment, the wetting body is configured as a micro-brush 50. The micro-brush 50 comprises a flocked portion so that numerous tousled brush hairs 52 extend outwardly.

The micro-brush 50 terminates in a substantially blunt end 54. This permits, as well, a force transmission or carryover of force to the bottom 26 of the narrow tube 14 and, thus, an insertion of the inner tube 14 to effect activation of the substance applying apparatus, if an engagement shoulder 56 is not provided.

As required, a reaction substance can be provided on the micro-brush 50, preferably in the manner of a salt deposited on the micro-brush. In this embodiment, a taper 60 or notch is provided underneath the engagement shoulder 56, which offers the possibility to bend the shaft 44 relative to the grip 42. In this configuration of the application element a plastic or permanent deformation is possible. It is also possible in this configuration to deform the bottom 26 of the inner tube via the deformation element 34 in order to initiate the wetting of the micro-brush 50 with the substance 20.

The present invention is, of course, in no way restricted to the specific disclosure of the specification and drawings, but also encompasses any modifications within the scope of the appended claims.

What is claimed is:

1. A substance applying apparatus for applying a substance to an application location; the apparatus comprising:
   an outer tube;
   a deformable inner tube received within the outer tube;
   an application element with a wetting body which is partially received in the inner tube;
   whereby, by application of pressure on the application element, a fluid connection between the inner space of the inner tube and the inner space of the outer tube is produced,
characterized in that
   a deformation body for effecting the asymmetrically deformation of the bottom of the inner tube is disposed within the outer tube;
   the inner tube being comprised of a softer material than the outer tube and,
   whereby upon application of pressure on the inner tube in a direction towards the bottom of the outer tube, at least the bottom of the inner tube is deformed.

2. A substance applying apparatus according to claim 1, wherein the inner tube includes side openings extending to adjacent the bottom, and the wall of the inner tube is deformable, at least to the openings.

3. A substance applying apparatus according to claim 1, the deformation element is provided with spaced apart wedges for deforming the inner tube upon the application of pressure of the application element.

4. A substance applying apparatus according to claim 3, wherein the wedges each comprise an angled surface which extends from the wall of the outer tube in an angled manner toward the inner tube.

5. A substance applying apparatus according to claim 1, wherein the deformation element is disposed at the end of the outer tube on one side thereof.

6. A substance applying apparatus according to claim 1, wherein the outer tube is comprised of a highly non-porous material such as glass.

7. A substance applying apparatus for applying a substance to an application location; the apparatus comprising:
   an outer tube;
   a deformable inner tube received within the outer tube;
   an application element with a wetting body which is partially received in the inner tube;
   whereby, by application of pressure on the application element, a fluid connection between the inner space of the inner tube and the inner space of the outer tube is produced,
characterized in that
   a deformation body for effecting the deformation of the bottom of the inner tube is disposed within the outer tube;
   the inner tube being comprised of a softer material than the outer tube and wherein a sealing lip extends outwardly at the bottom of the inner tube.

8. A substance applying apparatus according to claim 7, wherein the sealing lip is configured for sealing off the inner space of the outer tube from the inner space of the inner tube and is configured as a single unit on the inner tube.

9. A substance applying apparatus according to claim 7, wherein the sealing lip is at least partially deformable for permitting the flow of substances.

* * * * *